(12) United States Patent
Smith et al.

(10) Patent No.: US 8,456,628 B2
(45) Date of Patent: Jun. 4, 2013

(54) SPECTROSCOPY SYSTEM

(75) Inventors: Brian John Edward Smith, Dursley (GB); Richard William Bormett, Cherry Valley, IL (US)

(73) Assignee: Renishaw PLC, Wotton-Under-Edge (GB)

( * ) Notice: Subject to any disclaimer, the term of this patent is extended or adjusted under 35 U.S.C. 154(b) by 299 days.

(21) Appl. No.: 12/310,968

(22) PCT Filed: Oct. 11, 2007

(86) PCT No.: PCT/US2007/021705
§ 371 (c)(1),
(2), (4) Date: Mar. 13, 2009

(87) PCT Pub. No.: WO2008/045497
PCT Pub. Date: Apr. 17, 2008

(65) Prior Publication Data
US 2009/0310131 A1 Dec. 17, 2009

(30) Foreign Application Priority Data
Oct. 11, 2006 (GB) .................................. 0620141.2

(51) Int. Cl.
*G01J 3/44* (2006.01)
(52) U.S. Cl.
USPC ......................................................... 356/301
(58) Field of Classification Search
USPC .............................. 356/301; 359/15, 890, 485
See application file for complete search history.

(56) References Cited

U.S. PATENT DOCUMENTS

| 4,147,974 | A | * | 4/1979 | Greenwood | 324/304 |
|---|---|---|---|---|---|
| 4,606,054 | A | * | 8/1986 | Amitay et al. | 375/349 |
| 5,442,438 | A | | 8/1995 | Batchelder et al. | |
| 5,689,333 | A | * | 11/1997 | Batchelder et al. | 356/301 |
| 6,636,304 | B2 | * | 10/2003 | Gilby | 356/246 |
| 7,068,430 | B1 | | 6/2006 | Clarke et al. | |
| 7,239,782 | B1 | * | 7/2007 | Treado et al. | 385/117 |
| 2005/0185305 | A1 | | 8/2005 | Nishima et al. | |
| 2005/0248759 | A1 | * | 11/2005 | Wang et al. | 356/301 |
| 2006/0135861 | A1 | | 6/2006 | Lucassen et al. | |

FOREIGN PATENT DOCUMENTS

| JP | 01-287448 | 11/1989 |
|---|---|---|
| JP | A-1-287448 | 11/1989 |

(Continued)

OTHER PUBLICATIONS

Semrock, "Edge Filter Spectra vs. Angle of Incidence," http://www.semrock.com/Catalog/Raman_SpectrumvsAOl.htm, downloaded Mar. 23, 2006, pp. 1-4.

(Continued)

*Primary Examiner* — Tarifur Chowdhury
*Assistant Examiner* — Abdullahi Nur
(74) *Attorney, Agent, or Firm* — Oliff & Berridge, PLC

(57) ABSTRACT

A Raman spectroscopy system has a filter arrangement comprising two filters (16, 26A) in series, to reject light of the illuminating wavenumber from the scattered light of interest. The filters are tilted and have different characteristics for light of first and second different polarisation states. To counter this, the filters are arranged so that their respective effects on the respective polarisation states at least partially cancel each other out. This may for example be done by arranging their tilt axes (32, 34) orthogonally to each other.

6 Claims, 2 Drawing Sheets

FOREIGN PATENT DOCUMENTS

| | | |
|---|---|---|
| JP | A-2003-279899 | 10/2003 |
| JP | 2004-029438 | 1/2004 |
| JP | A-2004-29438 * | 1/2004 |
| JP | A-2007-93965 | 4/2007 |

OTHER PUBLICATIONS

Japanese Office Action mailed Jun. 29, 2012 in Japanese Patent Application No. 2009-532403 (with translation).

* cited by examiner

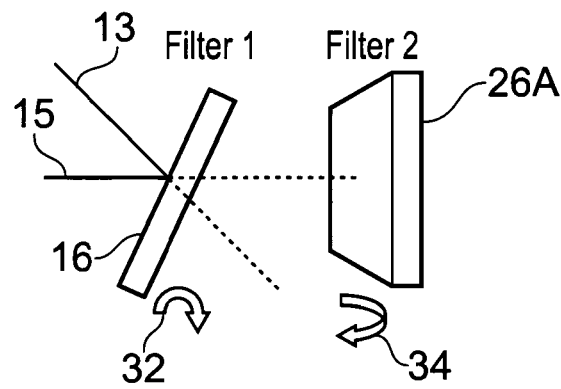
FIG. 2
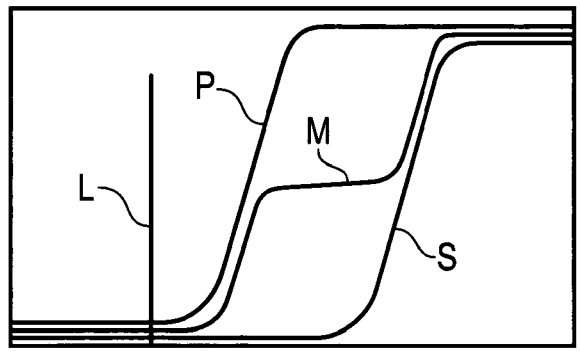
FIG. 3 — Filter 1
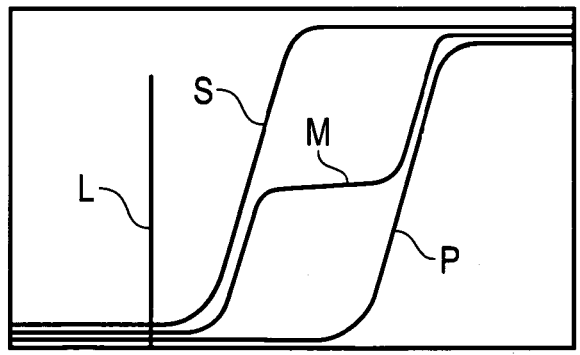
FIG. 4 — Filter 2
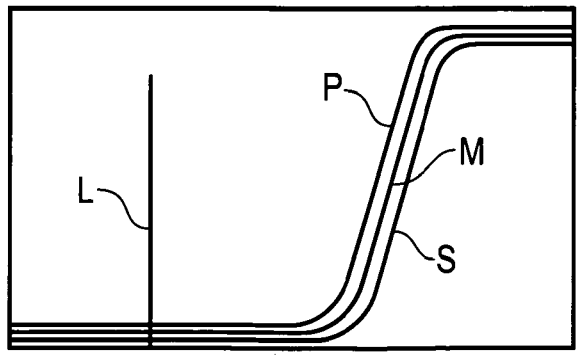
FIG. 5 — Filter 1 + Filter 2

SPECTROSCOPY SYSTEM

FIELD OF THE INVENTION

This invention relates to spectroscopy systems, for example, Raman spectroscopy systems.

BACKGROUND ART

A known Raman spectroscopy system is described in U.S. Pat. No. 5,442,438, which is incorporated herein by reference. FIG. 1 of the accompanying drawings shows a commercially-available embodiment of such a system.

In FIG. 1, light 13 from a laser source 10 is reflected by mirrors 12,14 and by a notch or edge filter 16 which acts as a dichroic beamsplitter. This directs it along an optical path 15 into a microscope 18, where it is deflected by a mirror 20 through an objective lens 22 and focused on a sample 24. Raman scattering takes place at the sample, producing Raman-shifted light at different wavenumbers from the incident laser line. The Raman-shifted light is collected by the objective lens 22 and passed back along the optical path 15 via the mirror 20 to the filter 16.

Whereas the filter 16 reflects light of the laser wavelength, it transmits the Raman-shifted wavenumbers. While doing so, it rejects the much more intense laser line. Further rejection of the laser line takes place in a second, identical filter 26. The Raman-shifted light then passes through a Raman analyser 28, which as described in U.S. Pat. No. 5,442,438 may comprise a diffraction grating, or filters which accept specific Raman lines of interest. The resulting light is then passed to a detector 30. This may for example comprise a charge-coupled device (CCD), across which a Raman spectrum may be dispersed by a diffraction grating. Or a filter may pass a two-dimensional image of the sample to the CCD, in light of a selected Raman wavenumber.

The notch or edge filters 16,26 may be holographic filters, as described in U.S. Pat. No. 5,442,438. Or they may be thin film multi-layer dielectric filters, such as for example the hard oxide filters supplied by Semrock Inc, Rochester, N.Y., USA under the trademark RazorEdge. Such filters are described in U.S. Pat. No. 7,068,430, incorporated herein by reference.

The filter 16 is necessarily placed at an angle to the optical path, in order to inject the light from the light source 10 towards the sample 24. However, in order to provide a sharp cut-off between the rejection of the laser line and the acceptance of Raman-scattered light at wavenumbers close to the laser line, U.S. Pat. No. 5,442,438 describes that this angle should be a low angle of incidence, such as 10°. The second filter 26 is similarly placed at the same low angle of incidence, to provide matching performance. In practice, angles of between 7.5° and 13° are used, but other angles are also possible.

Even at such low angles of incidence, however, polarisation effects reduce the sharpness of the cut-off. The larger the angle of incidence, the greater the problem. Specifically, the cut-off for p-polarised light is different from that for s-polarised light, by an amount which depends on the angle of incidence. It follows that the transmission characteristic of the filter shows a step or shelf in the cut-off edge at around 50% transmission for randomly polarised light. This results in polarisation artefacts in the resulting spectra measured by the device.

SUMMARY OF THE INVENTION

A first aspect of the present invention provides a spectroscopy system comprising:

a light source for illuminating a sample and causing scattering at wavenumbers shifted from that of the light source;

an optical path for collecting the scattered light and passing it to a detector;

a pair of filters in series in the optical path, arranged to reject light of the illumination wavenumber and accept light of the shifted wavenumbers, the filters having different characteristics for light of first and second different polarisation states;

characterised in that the filters are arranged so that their respective effects on the respective polarisation states at least partially cancel each other out.

A second aspect of the invention provides a filter arrangement, comprising:

a pair of filters in series in an optical path, arranged to reject light of a first wavenumber and accept light of a second wavenumber, the filters having different characteristics for light of first and second polarisation states;

characterised in that the filters are arranged so that their respective effects on the respective polarisation states at least partially cancel each other out.

Preferably, both filters are tilted about respective axes with respect to the optical path, the axes being generally orthogonal to each other.

BRIEF DESCRIPTION OF THE DRAWINGS

Embodiments of the invention will now be described by way of example, with reference to the accompanying drawings, wherein:

FIG. 2 shows a novel arrangement of a pair of filters in such a system;

FIGS. 3 and 4 are graphs of the transmission characteristics of the respective filters against wavenumber;

FIG. 5 is a graph of the combined transmission characteristic of the two filters.

DESCRIPTION OF PREFERRED EMBODIMENTS

The present embodiments of the invention are in most respects the same as described above with respect to FIG. 1. FIG. 2 illustrates one way in which FIG. 1 is modified, in a first embodiment of the invention.

Figure 1:
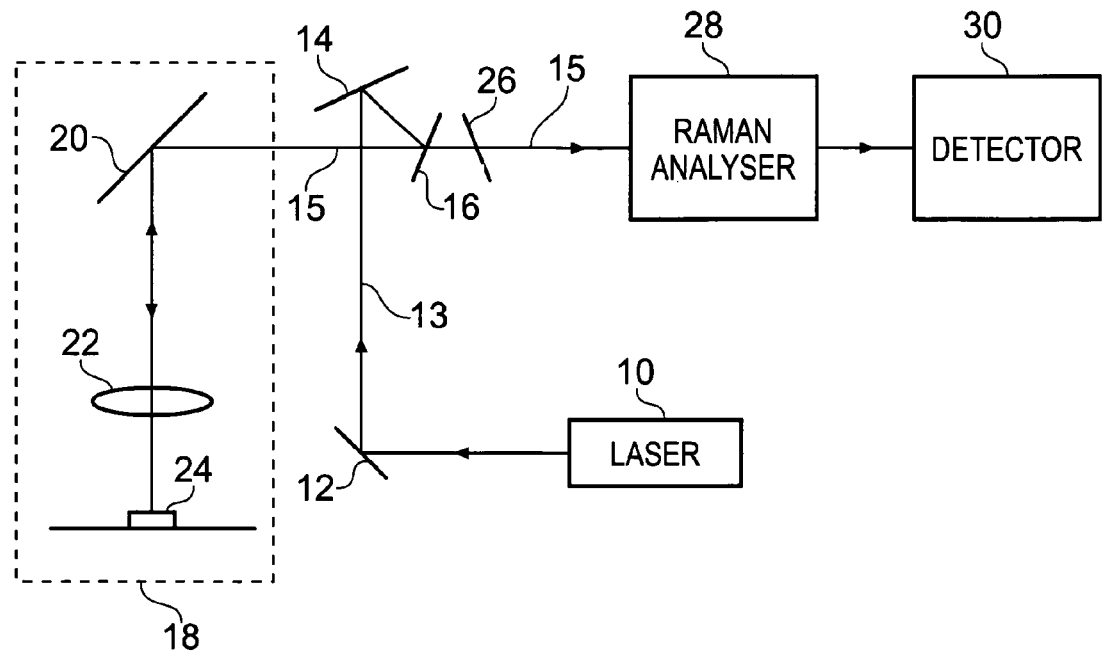
FIG. 1 is a schematic diagram of a prior art spectroscopy system.

The first notch or edge filter 16 is of the same type as in FIG. 1. It is arranged in the same way, tilted about an axis 32 with respect to the optical path 15, suitably at a low angle of incidence such as 10°. As described above, other angles may be used, such as between 7.5° and 13°, or even 450°. As shown in FIG. 2, the axis 32 is generally horizontal.

However, the second filter 26 is arranged differently, as shown at 26A in FIG. 2. Instead of being tilted about an axis parallel to the axis 32, it is tilted about an axis 34 which is generally orthogonal to the axis 32. Thus, the axis 34 is generally vertical. The second filter 26A is however preferably tilted to the same angle of incidence as the first, e.g. 10°. This ensures that its performance matches that of the filter 16, except as discussed below.

It would of course be possible to arrange the filters the other way around, so that the first filter was tilted about a vertical axis while the second filter was tilted around a horizontal axis. Any other substantially orthogonal arrangement could be used instead. Where the incident laser light 13 is to be injected into the optical path 15 by the filter 16, then of course it would need to be delivered to the filter 16 at an appropriate angle.

FIG. 3 shows the transmission characteristic (transmission versus wavenumber) of the first filter 16. It also shows the laser line L. In the following discussion, the s- and p-polarisation directions are all defined relative to the angle of incidence of the light as shown for the first filter 16 in FIG. 3.

As can be seen in FIG. 3, the transmission characteristic P for p-polarised light shows a sharp edge close to the laser line L. The transmission characteristic S of the s-polarised light has a similar sharp edge, but it is further away from the laser line L. As a result, the transmission characteristic M for light of mixed polarisation exhibits a flat shelf or step at around 50% transmission, because in this region the filter transmits p-polarised light but not s-polarised light.

In the prior art arrangement of FIG. 1, both the filter 16 and the filter 26 will exhibit characteristics similar to FIG. 3. Therefore, as discussed above, polarisation artefacts are introduced into the resulting spectra taken close to the laser line L. However, since the filter 26A in FIG. 2 is tilted about an axis which is orthogonal to the filter 16, the characteristics relative to s-polarised and p-polarised light are reversed. This is shown in FIG. 4, where the sharp cut-off edge S for the s-polarised light is closer to the laser line than the cut-off edge P for the p-polarised light.

Therefore, when the scattered light passes through the filters 16 and 26A in series as it travels along the optical path 15, the combined transmission characteristic is as shown in FIG. 5. The overall transmission characteristics S and P for the s-polarised and p-polarised light are much closer together. The resulting characteristic M for light of mixed polarisation therefore does not exhibit the shelf or step shown in FIGS. 3 and 4. The polarisation artefacts in the resulting spectra are reduced or eliminated.

In an advantageous arrangement, the axis of tilt (32 or 34) for the first filter 12 is chosen such that the rejection curve which is further from the laser line L matches the input laser polarisation. E.g. a filter with the FIG. 3 characteristic would be used when the laser is s-polarised. Or if the laser is p-polarised, then the axis of the first filter would be arranged so as to have the characteristic of FIG. 4. By adjusting the angle of incidence, the filter 12 can then be set so that its sharp rejection edge is closer to the laser line. The combined filters then give good laser rejection performance, whilst accepting Raman scattered light closer to the laser line than if the first filter was arranged with the other axis of tilt relative to the input laser polarisation.

The invention is not restricted to the use of filters tilted about orthogonal axes as shown in FIG. 2. Other arrangements may be envisaged to ensure that the effects of the two filters on the different polarisation states partially or wholly cancel each other out.

Figure 6:
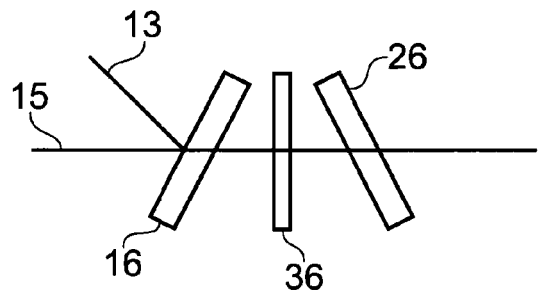
FIGS. 6 and 7 show further novel arrangements of filters for use in a system such as that of FIG. 1.

For example, such an arrangement is shown in FIG. 6. Here, there are two filters 16, 26, of any of the types mentioned above, and they are tilted to provide an angle of incidence as also discussed above. The tilt axes of the filters are parallel to each other, as in FIG. 1. However, a half-wave plate 36 is placed between the two filters. This rotates the polarisation of the scattered light in the path 15 by 90°, as it passes from one filter to the other. The effect is similar to the use of orthogonal tilt axes in FIG. 2.

Figure 7:
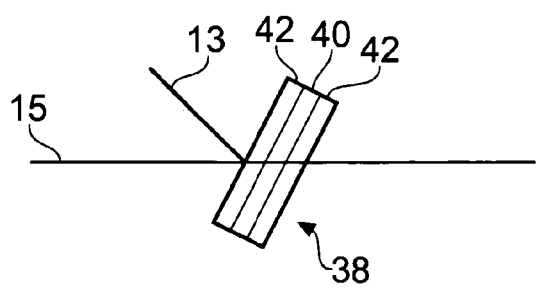

Alternatively, as shown in FIG. 7, a composite optical component 38 may be used. This comprises a half-wave plate 40, sandwiched between two filters 42. The filters 42 may be any of the types discussed above, and may simply be cemented on opposing faces of the half-wave plate 40. Advantageously, however, the filters 42 are of the thin film multi-layer dielectric type, e.g. of hard oxide as supplied by Semrock Inc. They may then be formed as coatings directly on the opposing faces of the half-wave plate 40.

If it is desired to return the light to its original polarisation state, a second half-wave plate could be included in the path 15, before or after the filter/half-wave plate arrangements shown in FIGS. 6 and 7.

The embodiments described may incorporate the various alternatives discussed above in relation to FIG. 1. In a further alternative, instead of the microscope 18, a remote sample may be analysed using a fibre optic probe of known type. With one type of such a fibre optic probe, the incident laser light may not be injected via the filter 16, but may instead be taken directly to the probe via a first optical fibre. The Raman scattered light is then returned to the filter 16 via a second optical fibre.

Furthermore, the system is not restricted to Raman spectroscopy. It may be used for other kinds of spectroscopic analysis, such as fluorescence, narrow-line photoluminescence and cathodoluminescence.

The invention claimed is:

1. A spectroscopy system comprising:
a light source for illuminating a sample such that scattering at wavenumbers shifted from an illumination wavenumber of the light source takes place at the sample;
a detector;
an optical path for collecting the scattered light and passing it to the detector; and
a filter arrangement, comprising:
a pair of filters in series in the optical path, arranged to reject light of the illumination wavenumber and accept light of the shifted wavenumbers, the pair of filters each being tilted with respect to the optical path at an angle of incidence such that each filter has a transmission characteristic for one of the first and second polarisation states having a cut-off edge closer to the illumination wavenumber than for the other of the first and second polarisation states, wherein
the pair of filters are arranged so that, the cut-off edges for one of the pair of filters relative to the other of the pair of filters for the first and second polarisation states are reversed such that overall transmission characteristics for the first and second polarisation states for the pair of filters combined are closer together than for each of the pair of filters individually.

2. A spectroscopy system according to claim 1, wherein the spectroscopy system is a Raman spectroscopy system.

3. A spectroscopy system according to claim 1, wherein a first one of the pair of filters is arranged to reflect light from the light source onto the sample.

4. A spectroscopy system comprising:
a light source for illuminating a sample such that scattering at wavenumbers shifted from an illumination wavenumber of the light source takes place at the sample;
a detector;
an optical path for collecting the scattered light and passing it to the detector; and
a filter arrangement, comprising:
a pair of filters in series in the optical path, arranged to reject light of the illumination wavenumber and accept light of the shifted wavenumbers, the pair of filters each being tilted with respect to the optical path at an angle of incidence such that each of the pair of filters has a transmission characteristic for one of the first and second polarisation states having a cut-off edge closer to the illumination wavenumber than for the other of the first and second polarisation states, wherein the pair of filters are arranged so that, for one of the pair of filters, the cut-off edge for the first polarisation state is closer to the illumination wavelength than the cut-off edge for the second polarisation state whereas, and for the other of the pair of filters, the cut-off edge for the second polarisation state is closer to the illumination wavelength than the cut-off edge for the first polarisation state such that overall transmission characteristics for the first and second polarisation states for the pair of filters combined are closer together than for each of the pair of filters individually.

5. A spectroscopy system according to claim 4, wherein the spectroscopy system is a Raman spectroscopy system.

6. A spectroscopy system according to claim 4, wherein a first one of the pair of filters is arranged to reflect light from the light source onto the sample.

\* \* \* \* \*